US006854599B2

(12) United States Patent
Ferrara, Jr. et al.

(10) Patent No.: US 6,854,599 B2
(45) Date of Patent: Feb. 15, 2005

(54) PACKAGING SYSTEM FOR FROZEN ALLOGRAFT TISSUE FORMS

(75) Inventors: Raymond G. Ferrara, Jr., Flemington, NJ (US); Babara Merboth, Bridgewater, NJ (US); Arthur A. Gertzman, Stony Point, NY (US)

(73) Assignee: Musculoskeletal Transplant Foundation, Edison, NJ (US)

(*) Notice: Subject to any disclaimer, the term of this patent is extended or adjusted under 35 U.S.C. 154(b) by 167 days.

(21) Appl. No.: 09/799,020

(22) Filed: Mar. 6, 2001

(65) Prior Publication Data

US 2002/0130093 A1 Sep. 19, 2002

(51) Int. Cl.[7] .............................................. A61B 17/06
(52) U.S. Cl. .................................... 206/438; 206/459.5
(58) Field of Search ................................ 206/775, 776, 206/777, 778, 438, 459.5; 229/103.3, 154, 148

(56) References Cited

U.S. PATENT DOCUMENTS

| | | | | |
|---|---|---|---|---|
| 2,022,906 A | * | 12/1935 | Weeks | 206/459.5 |
| 2,981,405 A | * | 4/1961 | Grasty | 206/784 |
| 3,346,168 A | | 10/1967 | Rouder | |
| 3,776,411 A | * | 12/1973 | Luckadoo | 220/503 |
| 4,046,311 A | * | 9/1977 | Voytko | 229/103.3 |
| 4,674,676 A | * | 6/1987 | Sandel et al. | 229/142 |
| 4,714,595 A | | 12/1987 | Anthony et al. | |
| 4,763,791 A | * | 8/1988 | Halverson et al. | 206/570 |
| 4,850,488 A | * | 7/1989 | Humbert | 206/459.5 |
| 4,863,052 A | * | 9/1989 | Lambert | 229/117.3 |
| 4,867,372 A | * | 9/1989 | Patterson | 229/141 |
| 5,040,677 A | * | 8/1991 | Tubo et al. | 206/440 |
| 5,503,324 A | * | 4/1996 | Bacchetti et al. | 229/112 |
| 5,924,625 A | * | 7/1999 | Klein et al. | 229/103.3 |
| 5,954,202 A | * | 9/1999 | Mellon | 206/462 |

* cited by examiner

Primary Examiner—Shian T. Luong
(74) Attorney, Agent, or Firm—John S. Hale; Gipple & Hale

(57) ABSTRACT

A container for storing and dispensing frozen allograft tissue packages comprising: a plurality of allograft tissue packages, a container housing for holding the plurality of frozen allograft tissue packages in a separated stacked array. The allograft tissue packages are of generally planar rectangular configuration with a waterproof coating to prevent the accumulation of moisture thereon with attenuate freezing of same and are provided with a window for viewing the contents therein and a label setting forth the contents of the package on an end wall of the allograft tissue package, the contents of the allograft tissue packages and labeling being viewable when mounted in shelving of the container housing. A plurality of horizontal shelves are mounted in the container housing parallel to each other and a plurality of vertical support members engage the shelves to support said shelves and serve as spacers for said shelves and to align the allograft tissue packages in a vertical and horizontal rows.

18 Claims, 4 Drawing Sheets

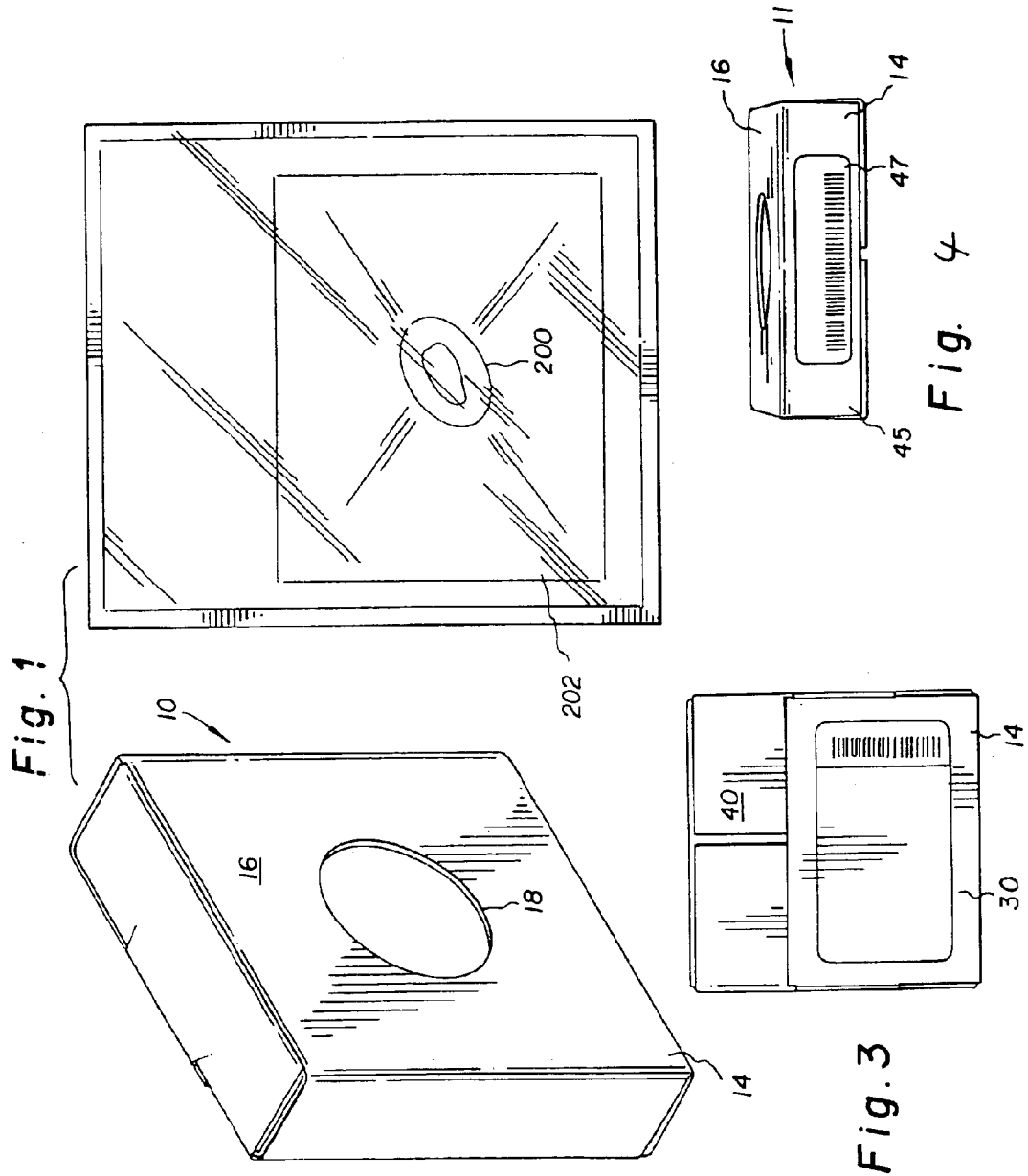

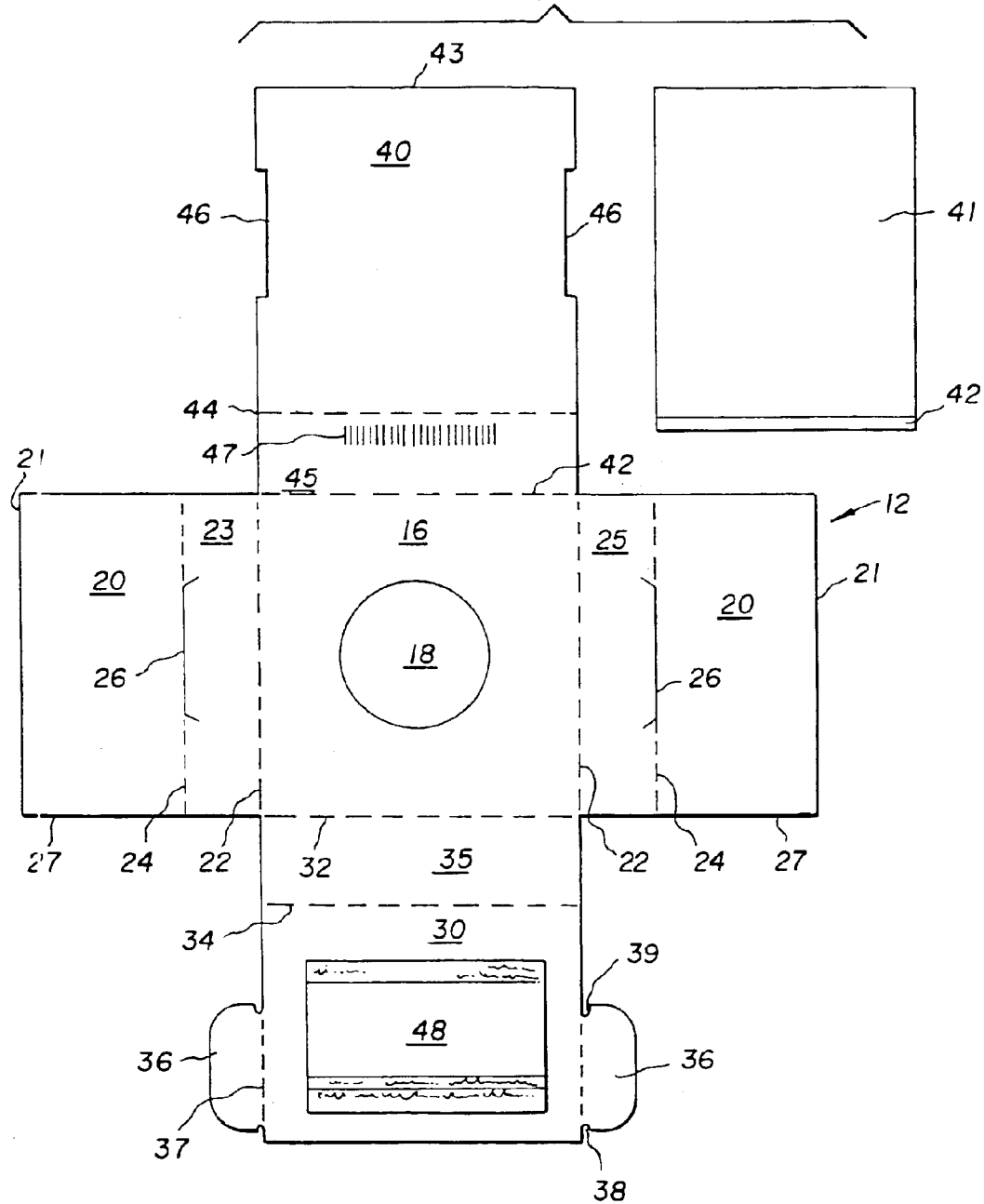

PACKAGING SYSTEM FOR FROZEN ALLOGRAFT TISSUE FORMS

CROSS-REFERENCE TO RELATED APPLICATIONS

There are no other applications related to the present application.

TECHNICAL FIELD OF THE INVENTION

The present invention generally relates to packaging for sterile tissue specimens for use in tissue transplant and more specifically to containers for packaged frozen allograft tissue forms and storage systems for same. The respective containers are configured to be used to store frozen allograft tissue forms in specifically designed boxes for small tissue forms and large tissue forms with a viewing window and label which does not frost over in the freezing chamber allowing the same to be easily viewed and read and recorded by optical scanning devices.

BACKGROUND OF TH PRIOR ART

Allograft tissue forms are useful in orthopaedic and neurosurgery. In practice, processed human tissue is delivered to the hospital and eventually to the surgeon in a form useful for surgical implantation. There are presently available a number of kinds of packaging for sterile specimens. One form of commonly used packaging is to provide the allograft tissue in a freeze-dried state, in a glass bottle with a stopper or other waterproof container. This type of packaging provides the advantage of stabilizing the tissue for storage in a warehouse or hospital supply room at normal room temperature conditions. Freeze-dried packaging works effectively for relatively small sizes of allograft tissues. Various types of tissue such as demineralized bone powders, chips, and small machined shapes such as pins, screws and spinal spacers are effectively packaged in this form. Currently there are no known effective tissue storage systems available for general use.

Large tissue forms cannot be effectively freeze-dried because their thickness and cross section is too great to allow for complete removal of moisture in the freeze-dry process. Such tissue forms include full form long bones e.g., femora, tibiae, humerii, fibulae and ilea and large cross sectional cuts of same. These large tissue forms require low temperature freezing in order to provide shelf life stability.

This frozen format is a serious problem for manufacturers of forms of allograft bone, and presents problems for the hospital and surgeon user, as effective storage to achieve tissue stability requires temperatures as low as −80° C. These low temperatures create problems for viewing, inventorying, and controlling the shipment of the individual packages of tissue forms. Specifically, the tissue form, when inspected or handled for shipping or selected for use, must be clearly seen by the user to select the right size, shape and condition of the bone for the specific surgery. Hence, this viewing requires some transparent element of the packaging to allow for visualization of the tissue. The deep frozen state and low temperatures required for tissue stability creates heavy moisture condensing on the packaging from the environmental air, which obscures the visualization of the tissue form. Current packaging uses transparent plastic bags with appropriate labeling and identification information to resolve this problem and provide suitable visibility. The use of plastic packaging in and of itself has problems because it is not convenient to store the irregularly shaped bone and consequently irregular shaped packaging that occurs from the plastic bags currently in use. This irregularity of the packaging shape makes for difficulty in storing the allograft tissue forms in low temperature freezers which are commercially available. The difficulty is manifested by requiring staff to sort through many bags in a freezer to find a specific individual tissue form of the right shape and size for the surgical use indicated causing potential problems as to the package sterility, integrity and recorded location. The condensation problem again comes into play where the contents, once removed from the freezer, will quickly condense over and make it difficult to read the labeling because of the low temperature condition and condensation that ensues from that system. Further, modern medical packaging includes bar code labeling to allow for automation of inventory control as well as maintaining a shipment and location trail for specific tissue forms. The tissue form package bar codes are also easily obscured by the condensation and frost that develops on packaging when the same are constantly shuffled causing exposure from the low temperature state to atmospheric conditions. As previously noted, condensation develops and unused packages put back into the freezer cause opaque frost to form over the labeling, which obscures the bar code and prevents it from being easily read by the automated machinery.

Accordingly, a packaging system has been developed to handle the various frozen form of allograft tissue which resolves these problems.

SUMMARY OF THE INVENTION

The present invention is directed toward a frozen allograft tissue package container storage dispenser assembly constructed to hold a plurality of specifically constructed frozen allograft tissue packages in a stacked array so that each package can be read as to its contents and the allograft tissue form viewed through a window in the package. The assembly housing defines an interior space with interior parallel shelving mounted therein and vertical spacer and support strips defining individual package compartments. Each allograft tissue package for either small tissue forms or large tissue forms includes a one piece blank of waterproof cardboard which is folded along fold lines to form a box with a precut viewing window and product identification labels.

It is an object of the invention to provide a packaging system which holds specially constructed tissue form boxes made of waterproofed corrugated paper with suitable openings so that the tissue can be visualized.

It is another object of the invention to provide a waterproof package having a viewing cutout for small tissue forms.

It is another object of the invention to provide a waterproof package having a viewing cutout for large tissue forms.

It is yet another object of the invention to provide labeling on designated panels of the tissue form packages so that they can be stacked like cassettes in a storage rack for easy visualization.

It is still another object of the invention to provide for a freezer organizer rack, which permits the waterproofed corrugated packages to be stacked and visualized from outside the freezer by a quick glance.

It is still another object of the invention to provide for a freezer organizer rack, which permits the waterproofed corrugated packages to be stacked and recorded by scanning apparatus.

In the accompanying drawings, there is shown illustrative embodiments of the invention from which these and other objectives, novel features and advantages will be readily apparent.

BRIEF DESCRIPTION OF THE DRAWINGS

FIG. 1 is a perspective view of the assembled small tissue form package container with the tissue pouch removed;

FIG. 2 is a plan view of the unfolded container blank for the small tissue form package container of FIG. 1 with the information pouch removed;

FIG. 3 is a bottom plan view of the assembled small tissue form package container shown in FIG. 1;

FIG. 4 is a side elevation view of the assembled small tissue form package container shown in FIG. 1;

DETAILED DESCRIPTION OF THE INVENTION

Figure 5:
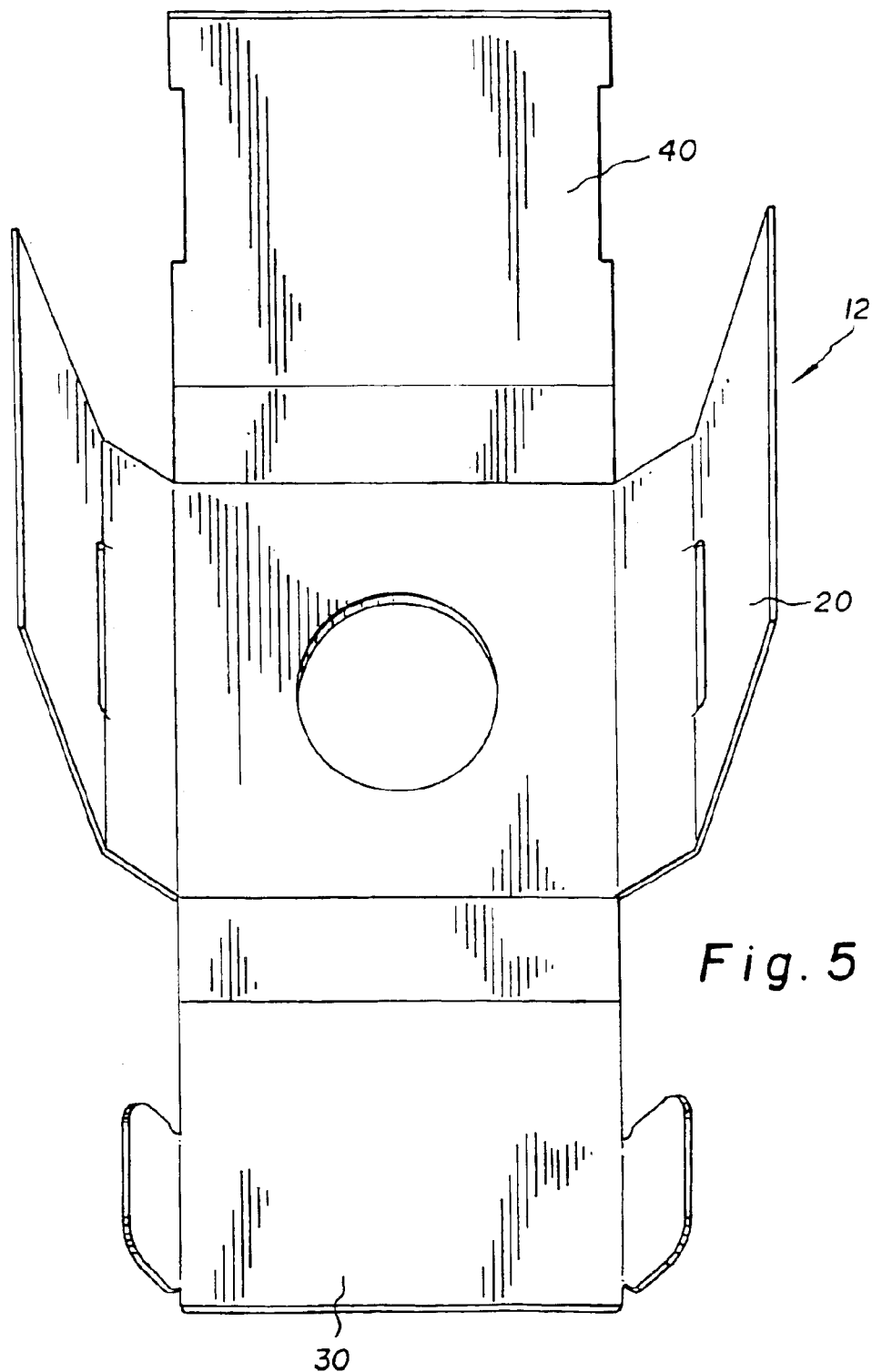
FIG. 5 is a perspective view of the interior of the partially folded blank of the small tissue form package container shown in FIG. 1.

The preferred embodiment and best mode of the tissue form package invention is shown in FIGS. 1–5. The component material used for the allograft tissue package 10 and the organizing shelf container 100 is made from a Michaelmann coated corrugated cardboard with a waterproof internal adhesive for the central label. This waterproofed corrugated material resists condensation from collecting on the surface and can be subjected to multiple freeze-thaw cycles through the very large temperature excursion required by the use of −80° C. freezing conditions. The temperature range change effecting the package could be as much as 110° C., from a −80° C. freezer to a +30° C. warehouse or storeroom area where the tissue may be selected for surgical use. The material selected for the shelf package 10 and organizing shelf container 100 could alternately be made of water-resistant plastics. Metal is not appropriate for the shelf container because metal, being a very good conductor of heat, will cause significant condensation and cause the packages to freeze to the metal rack. This is analogous to any commercial or residential freezer where the materials of the racks and chamber are plastic coated materials to prevent this kind of freezing and creating difficulty of removal of the contents.

The small graft tissue package 11 as shown in FIGS. 1–5 is constructed from a single blank 12 of waterproof paperboard. One side 14 of the paperboard blank is coated with a water resistant layer or chemical treatment. It is envisioned that a waterproofing resin can be used as the waterproofing material. A wide variety of resins such as recorcinol formaldehyde resins, urea formaldehyde resins and ketone aldehyde resins, e.g. acetone formaldehyde resins can be used for the waterproofing. The package blank 12 as shown in FIG. 2 has a central top panel 16 defining a throughgoing aperture 18 cut therein allowing the interior of the package, namely the tissue form 200 which is placed in a sterile pouch or bag 202 to be viewed. Rectangular side panels 20 extend from opposite sides of the central panel 16 and are provided with fold lines 22 and 24 which when folded form the sides 23 and 25 of the package. Fold lines 22 form the boundary between the top panel 16 and the sides. Both sides 23 and 25 have a throughgoing trapezoidal shaped slit 26 cut therein which receive the tab ears 36 of bottom panel 30. The bottom panel 30 is rectangular and extends outward from the central panel 16 between the side panels 20. The bottom panel 30 is provided with two fold lines 32 and 34 which when folded form another side 35 of the package. The bottom panel 30 is provided with opposing tabs 36 located near the distal end of the panel which extend outward from the sides of panel 30. Each tab 36 is provided with a fold line 37 allowing it to be folded or bent perpendicular with respect to the plane of panel 30 and to provide closure of the package when the tabs 36 are inserted into trapezoidal shaped slits 26. The tabs 36 are notched at 38 with an angular cut 39 leading to the notch to provide ease of folding. A second bottom panel 40 extends from the central panel 16 opposite bottom panel 30 and is provided with two fold lines 42 and 44 which when folded form the final side 45 of the package 11. The bottom panel 40 which is mounted under the bottom panel 30 defines opposing notches 46 on either side of the panel which when folded together with the trapezoidal slits 26 provide an entry for the tabs 36 when the package panels 30 and 40 are overlaid. The underside of the inner bottom panel 40 is provided with a water proof bag or pouch 41 which is secured to the underside of the panel by adhesive. The bag 41 preferably is plastic with a flexible transparent sheet which is crack resistant even at the low temperature used in the freezing process running abound −80° C. The bag 41 has one side with a peelable cover which can be peeled off to expose the adhesive so that the bag can be mounted to the surface of the lower top panel 40. The end of the bag 41 can be provided with an adhesive end seal 42 or a tongue and groove type fastener assembly. A bar code label 47 is adhesively secured to side 45. This label sets forth the part code, the item serial number and identifying bar code allowing easy inventory and tracking of the package to be undertaken. A product identification label 48 is adhesively secured to the top panel 30.

In assembly of the small tissue form container 11, panels 20 are folded on fold lines 22 and 24 to form sides 23 and 25 with the ends 21 of the panels 20 being positioned adjacent each other. Panel 40 is folded on fold lines 42 and 44 with the notches 46 overlying a slit formed by the fold line 24 and trapezoidal slit 26 of panels 20. End 43 of panel 40 is positioned adjacent the side edges 27 of panels 20 and overlies the outer surface of both side panels. Panel 30 has tabs 36 folded perpendicular along fold lines 37 and is mounted over the outer surface of panel 40 with the tabs 36 folded perpendicular along fold lines 37 and is mounted over the outer surface of panel 40 with the tabs 36 being inserted into slits formed by fold lines 24 and trapezoidal slit 26 of panels 20 to form an assembled package 11.

Figure 6:
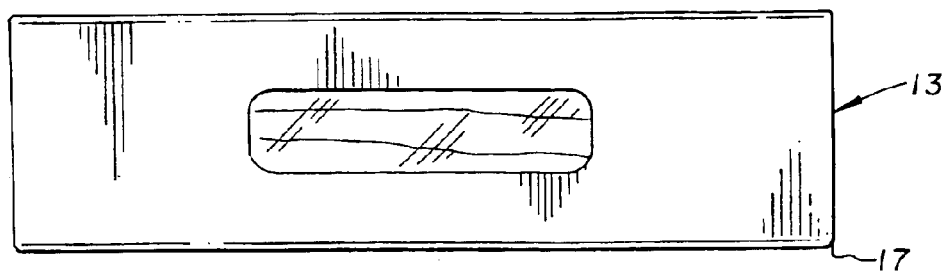
FIG. 6 is a perspective view of a package container for large allograft tissue forms.
Figure 7:
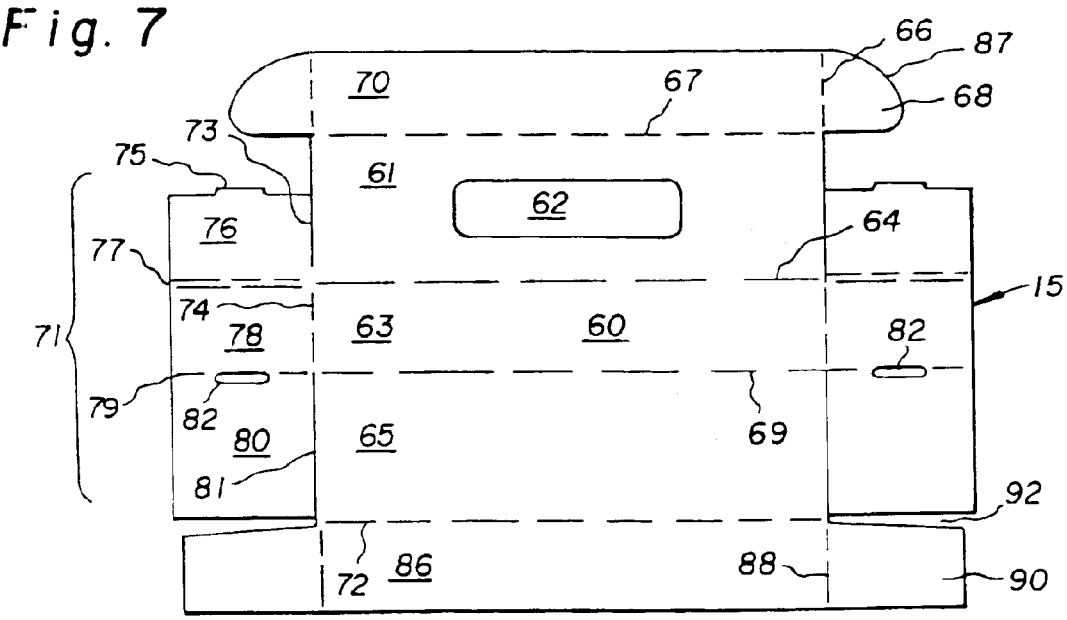
FIG. 7 is a plan view of the unfolded package container blank for the large tissue form container of FIG. 6.

The large tissue form container 13 as is seen in FIGS. 6 and 7 is constructed from a single blank 15 of waterproof paperboard with one side 17 being coated with a water resistant layer or chemical treatment. The blank 15 is formed with a central section 60 comprising a top cover panel, 61, a side panel 63 and a bottom panel 65. The top cover panel 61 defines a centrally located throughgoing elongated viewing aperture 62. The top cover panel 61 has a side fastening panel 70 with side tabs 68 located on opposite sides of the side fastening panel 70. Panel separation is achieved between the top cover panel 61 and the side fastening panel 70 by fold line 67. Each side tab 68 has a tab fold line 66 allowing the tab to bent at 90° to the plane of the panel 70. The side tab 68 has an outer curved surface 87 so that when the side tab is folded along the fold line 66, the tab surface is oriented transverse to the plane of the side fastening panel 71 which allow the rotation of tabs 68 into the side slots formed when the box structure is assembled A wing end panel assembly 71 extends from opposite ends of the central section 60 and are separated by double parallel fold lines 77 and a single fold line 79 to form three sections 76, 78 and 80. Section 76 is positioned adjacent top cover 61 but is separated from top cover 61 by cut 73 and defines an extending locking rib 75. Center section 78 is bounded by double parallel fold lines 77 and single fold line 79 which are respectively slightly offset from fold lines 64 and 69 of side 63 of the central section 60. Center section 78 is connected to side 63 by fold line 74 which allows folding of the wing panel assembly 71 into the center section. Lower section 80 defines a throughgoing rectangular aperture 82 located adjacent fold line 79 which receives locking rib 75 of section 76 when the box is folded. The lower section 80 is adjacent bottom panel 65 and is separated from bottom panel 65 by cut 81. A lower side panel 86 is formed integrally with central section 60 and extends outward from the central section bounded by fold line 72 and is provided with tab fold lines 88 which are transverse to the fold line 72 and inclined tab members 90 having an inner angled surface 92.

In assembly of the large tissue container 13, the top cover 61 and section 76 are folded over on fold lines 64 and 77. Side panel 63 is folded along fold line 69 with the middle section 78 being folded along fold line 79. The lower side panel 86 is folded on fold line 72 so that side panels 63 and 86 are parallel to each other and perpendicular to bottom panel 65. The angularly cut tab member 90 is folded along fold line 88 perpendicular to the plane of side panel 86. The end panel assembly 71 is folded along fold line 74 so that section 80 is overlapping bottom panel 65 and aperture 82 is located at the end of the container. The tab member 90 is adjacent to and parallel with section 78 which forms the end of the container. Section 76 is folded downward along double fold lines 77 with rib 75 fitting into the aperture 82 locking the assembly together. The tabs 68 are folded perpendicular to the plane of the side fastening panel 70 and are placed in the end assembly so that side panel 70 overlaps side panel 86 and the container is held in place.

Figure 8:
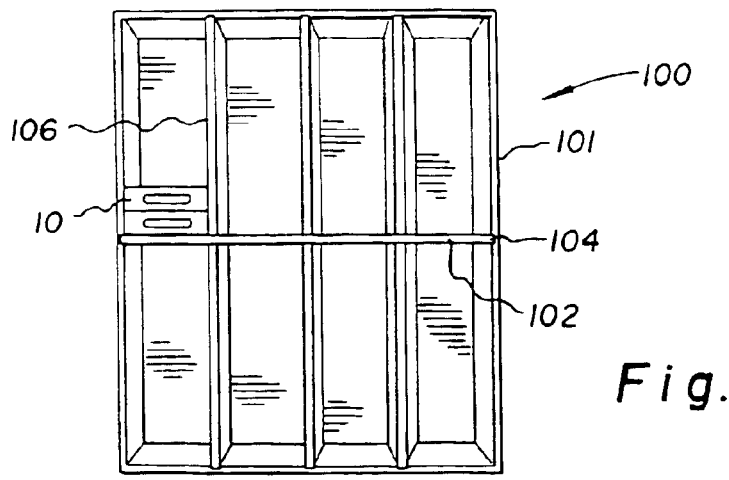
FIG. 8 is a perspective view of the shelf rack with a view of the tissue form package containers placed therein.

As seen in FIG. 8 a shelf container 100 for storing and dispensing frozen allograft tissue packages 10 holds the plurality of frozen allograft tissue packages in a separated stacked array. The allograft tissue packages being of generally planar rectangular configuration are stacked so that the planes of the individual packages are oriented in vertical and horizontal rows.

A plurality of horizontal shelves 102 are mounted in grooves 104 formed in the container housing 101 and a plurality of vertical support members 106 to engage and support the shelves 102 The horizontal shelves serve as spacers for said vertical support members 106, and to substantially align the allograft tissue packages 10 in a vertical and horizontal rows. As previously noted the allograft tissue packages are provided with a window 18/62 for viewing the contents therein and a label 44 setting forth the contents of the package on a side wall 45 of said allograft tissue package, the contents of said allograft tissue packages and labeling being viewable when mounted in said container housing A gas impermeable plastic bag 202 as seen in FIG. 1 which is heat sealed holds the tissue form 200 in a sterile environment. The sheet or sheet of plastic used in construction of the bag 202 can consist of single or multiple layers of desired thickness with the specific material chosen to provide a specific property such strength, gas permeability or impermeability, flexibility, puncture resistance and strength at low temperatures. The tissue containers 11 and 13 provide protection for the bag 202 to prevent the same from shattering or cracking during handling at the low freezing temperatures. Suitable plastics which can be used which work under the low temperature conditions are low-density polyethylene, high-density polyethylene, cross-linked, high-density polyethylene, polycarbonate, polysulfone, fluorinated ethylene polypropylene, ethylene-tetrafluoroethylene, ethylene-chlorotrifluoroethylene copolymer, perfluoroalkoyl, polyurethane.

A staff person selecting the tissue form can quickly find it because all the labels are provided in an organized, orderly array precluding the need to rummage through the freezer to pull each package, read each label, and find the individual package piece one was looking for. This reduces the time in which the freezer door will be open and reduces the condensation that develops as a result. Further, the waterproofed treatment to the corrugated carton prevents the adherence of the condensation to its surface. Subsequent replacement of the package into the freezer does not obscure the end label and its bar code because little to no water has settled on the surface and cannot, therefore, refreeze and block the view of the labeling.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present inventions defined by the following claims.

What is claimed is:

1. A container for storing frozen materials comprising:

a central rectangular panel defining a throughgoing aperture, two side panels integrally formed with said central panel located on opposite sides of said central panel, each of said side panels defining a fold line formed therein which forms a side edge of said central panel and a second fold line formed therein positioned a distance away from said first fold line and parallel to said first fold line to form a container side when folded with the distal ends of each side panel being adjacent each other when in a final folded position, a slot cut in each side panel substantially along said second fold line adapted to receive fastening tabs;

a first end panel extending from said central panel and integrally formed with said central panel, said first end panel having a fold line formed therein which forms a side edge of central panel and a second fold line formed therein positioned a distance away from said first fold line and parallel to said first fold line to form a container side when folded with the distal end of said first end panel defining a cutout with two stepped ends cut into opposing side walls, each cutout being positioned adjacent a respective side panel slot when in a final folded position with the stepped ends being adjacent a respective panel slot ends;

a second end panel extending from said central panel integrally formed with said central panel, said second end panel having a fold line formed therein which forms a side edge of central panel and a second fold line formed therein positioned a distance away from said first fold line parallel to said first fold line to form a container side when folded with the distal end of said second end panel overlapping said first end panel when in a final folded position, said second end panel defining fastening tabs extending outward from opposing side walls which are adapted to be inserted into said side panel slots and said first end panel cutouts holding said container in a stable assembled condition.

2. A container as claimed in claim 1 wherein all of said panels are waterproof.

3. A container as claimed in claim 2 wherein said panel waterproofing is a wax treatment.

4. A container as claimed in claim 2 wherein said panel waterproofing is a plastic treatment.

5. A container as claimed in claim 2 wherein said panel waterproofing is a chemical treatment.

6. A container as claimed in claim 1 wherein one of said container sidewalls is provided with an adhesive label having a product bar code and item identification.

7. A container as claimed in claim 1 wherein said first end panel has a transparent pouch secured to an underside surface.

8. A container as claimed in claim 7 wherein said transparent pouch has a peel away adhesive back panel and an openable top section which allows the insertion and removal of information materials.

9. A container as claimed in claim 7 wherein said transparent pouch is rectangular.

10. A container as claimed in claim 7 wherein said side panel slot is trapezoidal.

11. A container as claimed in claim 1 including a sterile permeable transparent plastic bag holding processed allograft tissue.

12. A container as claimed in claim 1 wherein said central rectangular panel aperture is circular.

13. A container for storing processed small allograft tissue under extreme freezing temperature conditions comprising:

a central rectangular panel defining a throughgoing aperture, two side panels integrally formed with said central panel located on opposite sides of said central panel, each of said side panels having a fold line formed therein substantially oriented along an axis of a side wall of said central panel and a second fold line formed therein positioned a distance away from said first fold line and parallel to said first fold line to form a container side when folded with the distal ends of each side panel being positioned adjacent each other when in a final folded position, a slot cut in each side panel substantially along said second fold line adapted to receive fastening tabs;

a first bottom panel extending from said central panel integrally formed with said central panel, said first bottom panel having a fold line formed therein substantially oriented along a side edge of central panel and a second fold line formed therein positioned a distance away from said first fold line and parallel to said first fold line to form a container side when folded with said first bottom panel defining a notch with stepped ends cut into opposing side walls which fit over respective side panel slots when in a final folded position, each notch being of a length to receive fastening tab from a second bottom panel;

a second bottom panel extending from said central panel integrally formed with said central panel, said second bottom panel having a fold line formed therein substantially oriented along a side edge of central panel and a second fold line formed therein positioned a distance away from said first fold line parallel to said first fold line to form a container side when folded with the distal end of said second bottom panel overlapping said first bottom panel when in a final folded position, said second bottom panel defining fastening tabs extending outward from opposing side walls which are adapted to be inserted into said side panel slots through said first bottom panel stepped notches, said fastening tabs being notched with an angular cut leading to each notch;

said central panel, side panels, first and second end panels having at least one waterproof surface.

14. A container as claimed in claim 13 wherein said side panel slot has a trapezoidal shape.

15. A container as claimed in claim 14 wherein said tabs have a notch cut at their base.

16. A container for storing processed small allograft tissue under extreme freezing temperature conditions comprising:

a central rectangular panel defining a throughgoing aperture, two side panels integrally formed with said central panel located on opposite sides of said central panel, each of said side panels having a fold line formed therein substantially oriented along an axis of a side wall of said central panel and a second fold line formed therein positioned a distance away from said first fold line and parallel to said first fold line to form a container side when folded with the distal ends of each side panel being positional adjacent each other when in a final folded position, a slot cut in each side panel positioned substantially along said second fold line adapted to receive fastening tabs;

a first bottom panel extending from said central panel integrally formed with said central panel, said first bottom panel having a fold line formed therein substantially oriented along a side edge of central panel and a second fold line formed therein positioned a distance away from said first fold line and parallel to said first fold line to form a container side when folded, said first bottom panel defining a stepped notch cut into opposing side walls, said stepped notches being positioned over said side panel slots with stepped ends of said notches being adjacent said side panel slots when in a final folded position and providing structured integrity for said container;

a second bottom panel extending from said central panel integrally formed with said central panel, said second bottom panel having a fold line formed therein substantially oriented along a side edge of central panel and a second fold line formed therein positioned a distance away from said first fold line parallel to said first fold line to form a container side when folded with the distal end of said second bottom panel overlapping said first bottom panel when in a final folded position, said second bottom panel defining fastening tabs extending outward from opposing side walls which are adapted to be inserted into said side panel slots through said first bottom panel stepped notches;

said central panel, side panels, first and second bottom panels having waterproof inside surface;

a transparent pouch with a peel away adhesive back panel and an openable top section which allows the insertion and removal of information materials is secured to an underside surface of one of said panels.

17. A container as claimed in claim 16 wherein said waterproof surface is a wax treatment.

18. A container as claimed in claim 16 wherein said waterproof surface is a plastic treatment.

* * * * *

UNITED STATES PATENT AND TRADEMARK OFFICE
CERTIFICATE OF CORRECTION

PATENT NO. : 6,854,599 B2
DATED : February 15, 2005
INVENTOR(S) : Raymond G. Ferrara, Jr., Barbara Merboth and Arthur A. Gertzman It is certified that error appears in the above-identified patent and that said Letters Patent is hereby corrected as shown below:

Title page,
Item [75], Inventors, the first name of inventor "Merboth" should read -- Barbara --.

Signed and Sealed this

Twelfth Day of July, 2005

JON W. DUDAS
*Director of the United States Patent and Trademark Office*